United States Patent [19]

Gementi et al.

[11] Patent Number: 4,977,291

[45] Date of Patent: Dec. 11, 1990

[54] PROCESS OF PRODUCING A SILANIC OR SILOXANIC COMPOUND CONTAINING AT LEAST ONE CYCLOALKYL RING

[75] Inventors: Francesco Gementi, Monza; Loris Sogli, Novara; Raffaele Ungarelli, Trecate, all of Italy

[73] Assignee: Istituto Guido Donegani S.p.A., Novara, Italy

[21] Appl. No.: 408,400

[22] Filed: Sep. 15, 1989

Related U.S. Application Data

[63] Continuation of Ser. No. 203,717, Jun. 2, 1988, abandoned.

[30] Foreign Application Priority Data

Jun. 5, 1987 [IT] Italy .............................. 41006 A/87

[51] Int. Cl.$^5$ ........................... C07F 7/08; C07F 7/10; C07F 7/18
[52] U.S. Cl. .................... 556/466; 556/413; 556/427; 556/425; 556/462; 556/473; 556/438; 556/440; 556/445; 556/449; 540/4; 540/128; 540/452; 540/487; 546/14; 544/69; 544/229; 548/110; 548/406; 548/955
[58] Field of Search ............... 556/466, 413, 427, 425, 556/462, 437, 438, 440, 445, 449; 540/4, 128, 452, 487; 544/69, 229; 546/14; 548/110, 406, 955; 549/4, 214

[56] References Cited

PUBLICATIONS

House, "Modern Synthetic Reactions", 2nd ed., W. A. Benjamin, Inc.; Menlo Park, CA (1972), pp. 6 to 10.
Morrison and Boyd, "Organic Chemistry", 3rd ed., Allyn & Bacon, Inc., Boston (1980), p. 286.

Primary Examiner—Paul F. Shaver
Attorney, Agent, or Firm—Stevens, Davis, Miller & Mosher

[57] ABSTRACT

A process of producing a silanic or siloxanic compound containing at least one cycloalkyl ring by the hydrogenation of a corresponding compound containing at least one aromatic ring, in the presence of a Raney nickel catalyst having a granulometry comprised essentially between 10 and 150 micrometers and a surface area of at least 80 m$^2$/g.

13 Claims, No Drawings

PROCESS OF PRODUCING A SILANIC OR SILOXANIC COMPOUND CONTAINING AT LEAST ONE CYCLOALKYL RING

This application is a continuation of application Ser. No. 203,717, filed June 2, 1988, now abandoned.

DESCRIPTION OF THE INVENTION

This invention relates to a process for producing a silanic or siloxanic compound containing at least one cycloalkyl ring by catalytic hydrogenation of a corresponding compound containing at least one aromatic or heteroaromatic ring and having the formula (I):

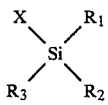

wherein:

X is an aryl, alkyaryl or arylalkyl group having from 6 to 20 carbon atoms, and optionally containing, in the chain or in the ring, at least one hetero-atom selected from oxygen, sulphur and nitrogen, and optionally, at least one halogen atom in place of a hydrogen atom; or the radical:

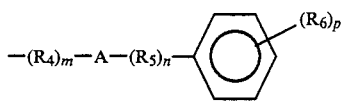

wherein $R_4$ and $R_5$, which may be same or different, are alkylene radicals containing from 1 to 20 carbon atoms, $R_6$ is an alkyl, alkoxyl, alcoholic, carboxyl, carboxyalkyl, or ester radical containing from 1 to 20 carbon atoms.

A is a heteroatom of the kind set forth above, m, n, and p are zero or an integer ranging from 1 to 10;

$R_1$, $R_2$, and $R_3$, which may be same or different, may have the same meaning as X or they may be hydrogen atoms, an alkyl or alkylene or alkoxy radical containing from 1 to 20 carbon atoms, a linear or branched alkyl radical having from 1 to 20 carbon atoms and containing one or more alkoxyl, carbonyl or carboxyl groups, or an $N(R_7)_2$ group in which $R_7$ is a hydrogen atom or an alkyl radical containing from 1 to 20 carbon atoms.

The catalytic hydrogenation of tolyl-triethoxy-silane having the formula (II)

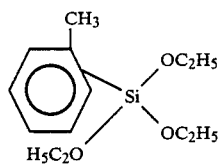

is known from the *Journal of the American Chemical Society*, Volume 84, May 20, 1962, pages 1856–1868. Such hydrogenation is carried out in the presence of a Raney nickel catalyst at a temperature ranging from 95° to 105° C. over 16 hours and at a pressure of 1,000 p.s.i., thereby obtaining a yield of about 50%.

That process is not industrially acceptable as far as both the yield and the productivity are concerned as well as the high pressures required for carrying out the hydrogenation. Moreover, it was observed that the yield level decreased to even lower values in the case of hydrogenation of some aryl alkoxy-silanes that are highly useful from an industrial point of view, by using the same operating conditions described in the above-mentioned publication. Moreover, it was virtually impossible, till now, to avoid a massive hydrogenolysis of the carbon-silicon bonds.

It has now been discovered, in accordance with the present invention, that there is a particular kind of Raney nickel catalyst that leads to excellent and quite unexpected yields, not only in the case of the specific tolyl-triethyoxysilane of the formula (II), but also more generally in the case of silanic or siloxanic compounds of the formula (I), which, till now, could not be hydrogenated, or were hydrogenated only at the expense of negligible yields with considerable losses owing to hydrogenolysis and under burdensome operating conditions.

Therefore this invention, in its widest aspect, relates to a process for producing a silanic or siloxanic compound containing at least one cycloalkyl ring by catalytic hydrogenation of a corresponding aromatic or hetero-aromatic derivative of the formula (I), wherein the catalyst is a particular type of Raney nickel.

According to the present invention, the hydrogenation of the silanic or siloxanic compound of formula (I), containing at least one aromatic or hetero-aromatic ring is carried out in solution, at a pressure of at least 2 bar and in the presence of a catalytic amount of Raney nickel catalyst having a granulometric distribution comprised essentially between 10 and 150 micrometers and a surface area of at least 80 m²/g.

Preferably, the Raney nickel catalyst used in the process of the present invention has a granulometric distribution between 10 and 150 micrometers with a content lower than 10% by weight of particles having dimensions lower than 10 micrometers, and a content lower than 10% by weight of particles having dimensions higher than 150 micrometers.

The average dimensions of the catalyst particles are about 50 micrometers.

Moreover, the Raney nickel catalyst used in the process of the present invention has preferably a surface area between 80 and 100 m²/g.

The catalyst may be prepared according to one of the conventional methods which may be found in the literature such as, for example, Kirk-Othmer, *Encyclopedia of Chemical Technology*, Vol. 5, pages 22–25, Ed. J. Wiley & Sons Inc. (1979), starting from an alloy containing at least 20%, and preferably from 25 to 45% by weight of $NiAl_3$.

This type of Raney nickel catalyst is well known on the market and is produced and sold by the Grace Company, USA, under the trademark "Nickel Raney 4200".

According to the process of the present invention, the hydrogenation is carried out in the presence of an organic solvent, preferably an apolar solvent, such as for instance a saturated hydrocarbon, such as n-hexane or cyclohexane.

The amount of solvent ranges generally from 0.1 to 10 Kg per Kg of product of the formula (I).

The amount of catalyst to be used in the process of the present invention is not critical and may range from 5 to 300 g of Raney nickel catalyst per Kg of the product of the formula (I) that is to be hydrogenated.

According to a preferred embodiment, the hydrogenation is carried out at temperatures between 50° and 150° C., at a pressure ranging from 2 to 100 bar, preferably from 5 to 50 bar, and with a reaction time between 0.5 to about 50 hours, and preferably between 1 and 20 hours.

The commercial importance of the invention will be even more appreciated considering that the cycloalkyl derivatives of silanes and siloxanes were obtained industrially through a complicated process that used cyclohexene as the raw starting material; see on this subject the article in the *Journal of Organometallic Chemistry*, Vol. 121 (1976), page 40.

A non-limiting list of silanes and siloxanes which may be obtained by the process of the present invention is as follows:

(cyclohexyl)-Si—(OCH$_3$)$_3$;
(cyclohexyl)$_2$-Si—(OCH$_3$)$_2$;

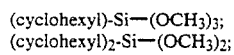

(cyclohexyl)-Si(OC$_2$H$_5$)$_3$;
(cyclohexyl)$_2$-Si—(OC$_2$H$_5$)$_2$;

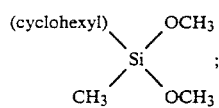

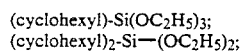

1,3-dicyclohexyl-tetramethyl-disiloxane;
tetracyclohexyl-oxysilane;
tetracyclohexyl-silane; and
cyclohexyl-methylene-trimethyl-silane.

The silanes and siloxanes obtained according to the present invention may be used advantageously for preparing catalysts for olefine polymerization.

The following examples will illustrate the invention without limiting its scope.

EXAMPLES 1-3

An amount, as set forth in Table 1, of the Raney nickel catalyst, sold by the Grace Company as "Nickel Raney 4200", having the following granulometric distribution: 5% lower than 10 micrometers, 30–35% lower than 42 micrometers, 60–65% lower than 150 micrometers, and a surface area of 80–100 m$^2$/g, was loaded, in the form of a suspension in a solvent, into an autoclave having a volume of 500 cm$^3$. Then there was added methyl-phenyl dimethyoxysilane and solvent in the amounts set forth in Table 1.

The mixture was heated gradually over a period of one hour, under strong stirring, at a temperature and hydrogen pressure as set forth in Table 1. After the reaction time indicated in Table 1, the hydrogenation was substantially complete. The final mass was cooled, the catalyst was separated by decantation and filtration, and the solvent was evaporated.

Methyl-cyclohexyl-dimethoxysilane was obtained having a degree of purity as determined by gas-chromatography, and in the amount and yields as set forth in Table 1.

TABLE 1

| Examples | 1 | 2 | 3 |
|---|---|---|---|
| Catalyst (g) | 22 | 1 | 30 |
| Methyl-phenyl-dimethoxy silane (MPS) (g) | 146 | 120 | 100 |
| Solvent | n-hexane | ethyl acetate | n-hexane |
| T (°C.) | 90–95 | 100 | 85 |
| H$_2$ Pressure (bar) | 16 | 30 | 5 |
| Catalyst/MPS ratio (g/Kg) | 150 | 8 | 300 |
| Solvent/MPS ratio (Kg/Kg) | 0.9 | 1 | 2 |
| Time (hours) | 5 | 10 | 10 |
| Methyl-cyclohexyl-dimethoxysilane (g) | 147.6 | 130 | 101.7 |
| Purity (%) | 98.9 | 75 | 99.5 |
| Yield | 98 | 79 | 98 |

EXAMPLES 4 to 8

By operating according to the procedure of the preceding examples and by using the same catalyst, the hydrogenation of other silane or siloxane derivatives of the formula (I) was carried out. In Table 2 there are reported the compounds subjected to hydrogenation, the catalyst amounts, the solvent type, the pressure, the temperature, the reaction time, as well as the products obtained and the relevant amounts and yields:

TABLE 2

| Examples | 4 | 5 | 6 | 7 | 8 |
|---|---|---|---|---|---|
| Catalyst (g) | 25 | 20 | 20 | 10 | 1 |
| Di-phenyl-dimethoxy silane (g) | 150 | — | — | — | — |
| Phenyl trimethoxy silane (g) | — | 100 | — | — | — |
| Phenyl triethoxy silane (g) | — | — | 100 | — | — |
| Benzyl trimethyl silane (g) | — | — | — | 150 | — |
| 1,3-diphenyl-tetramethyl disiloxane | — | — | — | — | 150 |
| Solvent | cyclo-hexane | n-hexane | cyclo-hexane | n-hexane | n-hexane |
| Temperature (°C.) | 95 | 105 | 105 | 90 | 110 |
| H$_2$ Pressure (bar) | 12 | 14–16 | 10 | 20 | 35 |
| Catalyst/silane ratio (g/Kg) | 167 | 200 | 200 | 67 | 7 |
| Solvent/silane ratio (Kg/Kg) | 1 | 0.9 | 1 | 1.1 | 1 |
| Time (h) | 8 | 6 | 5 | 9 | 10 |
| Di-cyclohexyl-dimethoxy silane (g) | 155.6 | — | — | — | — |
| Cyclohexyl trimethoxy silane (g) | — | 102.5 | — | — | — |
| Cyclohexyl triethoxy silane (g) | — | — | 97.5 | — | — |
| Cyclohexyl methylene-trimethyl silane (g) | — | — | — | 150.8 | — |
| 1,3-dicylcohexyl-tetramethyldisiloxane (g) | — | — | — | — | 157.8 |
| Yield (%) | 97.5 | 97 | 91 | 96 | 91 |
| Purity (%) | 98.5 | 97.5 | 95.7 | 99 | 90.5 |

What is claimed is:

1. A process of producing a silanic or siloxanic compound containing at least one cycloalkyl ring by the catalytic hydrogenation of a corresponding silanic or siloxanic compound containing at least one aromatic or heteroaromatic ring having the formula (I):

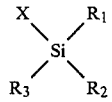 (I)

wherein:
X is an aryl, alkylaryl or arylalkyl group having from 6 to 20 carbon atoms, optionally containing, in the chain or in the ring, at least one heteroatom selected from oxygen, sulphur and nitrogen and, optionally, at least one halogen atom in place of a hydrogen atom; or the radical

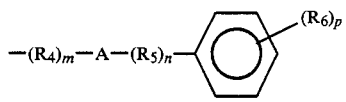

wherein
$R_4$ and $R_5$, which may be same or different, are an alkylene radical containing from 1 to 20 carbon atoms,
$R_6$ is an alkyl, alkoxyl, hydroxyalkyl, carboxyalkyl, carboxyl or ester radical containing from 1 to 20 carbon atoms,
A is a heteroatom of the kind set forth above, and
m, n, and p are zero or an integer ranging from 1 to 10;
$R_1$, $R_2$ and $R_3$, which may be same or different, may have the same meaning as X, or may be a hydrogen atom, an alkyl, alkylene or alkoxy radical containing from 1 to 20 carbon atoms, a linear or branched alkyl radical having from 1 to 20 carbon atoms and containing one or more alkoxyl, carbonyl or carboxyl groups of an $N(R_7)_2$ group, in which $R_7$ is hydrogen atom or an alkyl radical containing from 1 to 20 carbon atoms, characterized in that the hydrogenation is carried out in solution, at a pressure of at least 2 bar and in the presence of a catalytic amount of Raney nickel catalyst having a granulometric distribution comprised essentially between 10 and 150 micrometers and a surface area of at least 80 m²/g.

2. A process according to claim 1, wherein the Raney nickel catalyst has a content lower than 10% by weight of particles having dimensions lower than 10 micrometers and a content lower than 10% by weight of particles having dimensions higher than 150 micrometers.

3. A process according to claim 1 or 2, wherein the Raney nickel catalyst has a surface area between 80 and 100 m²/g.

4. A process according to claim 1 or 2, wherein the Raney nickel catalyst is obtained starting from an alloy containing at least 20% by weight of $NiAl_3$.

5. A process according to claim 1 or 2, wherein the Raney nickel catalyst is obtained starting from an alloy containing from 25 to 45% by weight of $NiAl_3$.

6. A process according to claim 1 or 2, wherein the catalyst employed is between 5 and 300 g per Kg of the compound that is to be hydrogenated.

7. A process according to claim 1 or 2, wherein the hydrogenation is carried out in a solution of an organic solvent, the solvent being present in an amount of from 0.1 to 10 Kg per Kg of the compound that is to be hydrogenated.

8. A process according to claim 7, wherein the solvent is apolar.

9. A process according to claim 7, wherein the solvent is n-hexane or cyclohexane.

10. A process according to claim 1 or 2, wherein the hydrogenation is carried out at a temperature of from 50° to 150° C. and with a reaction time from 0.5 to 50 hours.

11. A process according to claim 1 or 2, wherein the hydrogenation is carried out at a temperature of from 50° to 150° C. and with a reaction time from 1 to 10 hours.

12. A process according to claim 1 or 2, wherein the hydrogenation is carried out at a hydrogen pressure between 2 and 100 bar.

13. A process according to claim 1 or 2, wherein the hydrogenation is carried out at a hydrogen pressure between 5 and 50 bar.

* * * * *